United States Patent [19]

Brown

[11] Patent Number: 5,103,063
[45] Date of Patent: Apr. 7, 1992

[54] INTERMEDIATES USEFUL FOR THE CHIRAL ISOPRENYLATION OF ALDEHYDES

[75] Inventor: Herbert C. Brown, West Lafayette, Ind.

[73] Assignee: Aldrich Chemical Company, Inc., Milwaukee, Wis.

[21] Appl. No.: 562,245

[22] Filed: Aug. 3, 1990

[51] Int. Cl.$^5$ ............................................. C07F 5/02
[52] U.S. Cl. ................................................... 568/1
[58] Field of Search ........................................... 568/1

[56] References Cited

U.S. PATENT DOCUMENTS 4,713,380 12/1987 Brown ..................................... 568/1
4,978,794 12/1990 Brown ..................................... 568/1

Primary Examiner—Marianne Cintins
Assistant Examiner—Margaret Argo

[57] ABSTRACT

An improved process for preparing either optically pure enantiomer of the bark beetle pheromones ipsenol and ipsdienol is provided. The process is also applicable to the condensation of aldehydes of widely varying properties to the corresponding chiral alcohol. This invention also concerns novel intermediates R'$_2$B(2'-isoprenyl) wherein R' is isopinocampheyl, 2-isocaranyl and 4-isocaranyl.

4 Claims, No Drawings

INTERMEDIATES USEFUL FOR THE CHIRAL ISOPRENYLATION OF ALDEHYDES

BACKGROUND OF THE INVENTION

The present invention relates to an improved synthesis of both enantiomers of ipsenol and ipsdienol in high optical purity and in good yields, as well as an improved method for the isoprenylation of aldehydes and novel intermediates therefor.

Bark beetles of the Ips genus are major pests in conifer forests and are responsible for mass attacks in pine forests. These beetles signal aggregation and colonization by phermonal communication which involves three terpene alcohols, ipsenol (2-methyl-6-methylene-2,7-octadien-4-ol), ipsdienol (2-methyl-6-methylene-7-octen-4-ol) and cis-verbenol. The absolute configurations of the terpene alcohols identified as the principal components of these attractants have been determined as (S)-(−)-ipsenol, (S)-(+)-ipsdienol and (1S, 4S, 5S)-cis-verbenol. Their antipodes are biologically inactive. See for example J. Vité et al. *Nature*, Vol. 272, pp. 817–818 (27 Apr. 25, 1978); R. Silverstein et al., *Science*, Vol. 54, pp 509–510 (28 Oct. 1966).

The five-spined engraver beetle, *Ips grandicollis*, aggregates only in response to (S)-ipsenol, both ipsenol and ipsdienol constitute aggregation pheromones of the spruce-infesting bark beetle, *Ips typographus* and ipsdienol is present in the population attractant of *Ips sexdentatus*.

Because these compounds are important as lures for attracting and trapping these pests on a large scale, various investigators have attempted to develop satisfactory processes for the production of the biologically active isomers.

Many syntheses of racemic ipsenol and ipsdienol are available in the literature. See for example, Bubnov, Yu et al., *Tetrahedron Lett.* 1987, 26, 2797; Silverstein, R. M. et al., *Science*, 1966, 154, 509; Karlsen, S. et al., *Acta chem. Scan. B*, 1970, 30, 664; Cazes B. et al., *J. Organometal Chem.* 1979, 177, 67; A. Hosomi et al., *Tetrahedron Leters*, 1979, 429; Y. Masaki et al., *J. Chem. Soc. Perkin Trans.I*, 1984, 1289; and Klusener, P. A. A. et al., *J Org. Chem.* 1987, 52, 5261.

Mori first synthesized both of these pheromones in optically active form and assigned their configurations. Mori's initial synthesis of ipsenol, starting from leucine, was both lengthy and cumbersome and resulted in low chemical ( about 5%) and optical yields (80%). K. Mori: *Tetrahedron Lett.* 1975, 2187; K. Mori: *Tetrahedron* 1976, 32, 1101. Later, Mori modified his procedure to obtain optically pure ipsenol ($\geq 99\%$) but the overall yield still remained low. Ipsdienol starting from (R)-malic acid gave 90% ee for the pheromone. K. Mori: *Tetrahedron Lett.* 1976, 1609; K. Mori et al., *Tetrahedron* 1979, 35, 933.

Additional enantioselective syntheses have since been reported. Ohloff et al. prepared ipsdienol in 91% ee (R) and 80% ee (S) from the enantiomers of verbenone via the corresponding β-pinene-4-ols, G. Ohloff et al.: *Helv. Chim Acta.* 1977, 60, 1496. Norin prepared racemic ipsdienol via sensitized photooxidation of commercially available myrcene followed by acid catalyzed rearrangement, P. Baeckström et al.: *Acta Chem. Scand. B.* 1983, 37, 1. Oxidation of the tertiary alcohol obtained from photooxidation to myrcenone, followed by asymmetric reduction of the carbonyl moiety using Noyori's Binal-H (*J. Am. Chem. Soc.*, 1984, 106, 6709, 6717) provided both enantiomers of ipsdienol in 63% ee. Modified Binal-H provided ipsdienol of even lower optical purity. P. Baeckström et al, supra. H. Yamamoto's condensation of isovaleraldehyde with the tartrate ester of allenyl boronic acid provided the corresponding homopropargylic alcohol which was further elaborated to the 2-brominated alcohol. Protection of the alcohol as the tetrahydropyranyl ether followed by treatment with the vinyl Grignard reagent and deprotection furnished (−) ipsenol in $\geq 99\%$ ee. See N. Ikeda et al., *J. Am. Chem. Soc.* 1986, 108, 143.

Despite the substantial efforts of numerous investigators, prior art procedures are generally expensive, multistepped processes that produce the desired opticals in low yields and/or low optical purity. The present invention provides an elegant process for producing these important pheromones in high optical purity and excellent yields compared with the prior art.

SUMMARY OF THE INVENTION

The present invention provides a one-pot reaction sequence for the facile synthesis of either enantiomer of ipsenol or ipsdienol. The process is equally applicable to the isoprenylation of other aldehydes of varying steric and electronic environments.

Generally speaking, the process of this invention for synthesizing either enantiomer of ipsenol or ipsdienol in $\geq 96\%$ ee comprises treating (reacting) isovaleraldehyde or β,β-dimethylacrolein, respectively with $^d$Ipc$_2$B(2'-isoprenyl) and $^l$Ipc$_2$B(2'-isoprenyl), depending upon the desired end product. The process is represented by the following reaction scheme:

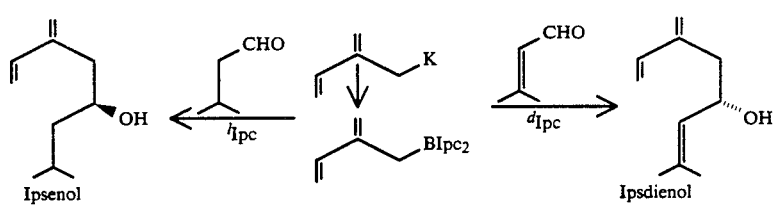

Ipsenol          Ipsdienol

Generally speaking, B-2'-isoprenyldiisopinocampheyl boranes, $^{d\ or\ l}$Ipc$_2$BIpn, respectively, are synthesized by the reaction of 2'-isoprenylpotassium with B-methoxydiisopinocampheyl borane ($^{d\ or\ l}$Ipc$_2$BOMe) followed by treatment with BF$_3$.EE according to the following reaction scheme:

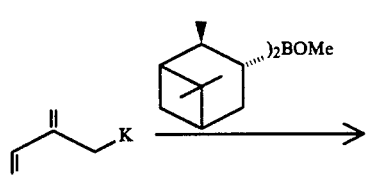

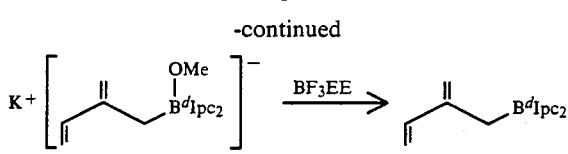

Condensation of the B-2'-isoprenyldiisopinocampheylborane with aldehydes provides the corresponding chiral homoallylic alcohols as illustrated in the examples which follow.

Generally speaking, the above general method was applied to the preparation of both enantiomers of the pheromones ipsenol and ipsdienol by reacting the stereoisomers of B-2'-isoprenyldiisopinocampheylborane with isovaleraldehyde and β,β-dimethylacrolein, respectively. In this case, the product alcohols were isolated by a non-oxidative workup, i.e. addition of acetaldehyde to the reaction mixture, converting the borinate intermediate to the corresponding boronate, with simultaneous displacement of α-pinene. Addition of diethanolamine precipitated the boron components and the products were isolated from the filtrate by distillation.

In another embodiment, the present invention provides a general process for the synthesis of diterpenyl-(2'-isoprenyl)borane, R'$_2$B(2'-isoprenyl), wherein R' is isopinocampheyl, 2-isocaranyl and 4-isocaranyl and comprising metallating isoprene to form $H_2C=C(CH_2K)-CH=CH_2$ and attaching the 2'-isoprenyl group to the boron of a (terpenyl)$_2$BX derivative, wherein X is selected from the group comprising OR, OMe, F, Cl, Br or I, wherein R is alkyl. The terpene may be selected from the group consisting of α-pinene, 3-carene and 2-carene.

The process of this invention may be employed for the chiral isoprenylation of aldehydes by reacting the desired aldehyde with a compound of the formula R'$_2$B(2'-isoprenyl) wherein R' is isopinocampheyl, 2-isocaranyl and 4-isocaranyl.

The intermediates R'$_2$B(2'-isoprenyl) are novel compounds.

DETAILED DESCRIPTION OF PREFERRED EMBODIMENTS

Techniques for handling air-sensitive compounds, as described by H. C. Brown et al., *Organic Synthesis via Boranes*, Wiley Interscience: New York, 1975, Chapter 9, incorporated by reference herein, were followed. Spectroscopic measurements ($^1$H and $^{11}$B NMR and IR) were made with standard instruments. GC analyses were done on a Varian Aerograph Series 1200 gas chromatograph having a flame ionization detector and integrated with a Hewlett-Packard 3380 S integrator. GC columns, ⅛"×12', were packed with 10% SP-2100 (Supelco, Inc.) on Chromosorb W (Supelco, Inc.,(-80-100 mesh) or 5% Carbowax 1540 (Supelco, Inc.) on Chromosorb W (80-100 mesh). Analyses of the MTPA esters or MCF derivatives were performed on a Hewlett- Packard 5890A gas chromatograph using a Supelcowax glass capillary column (15 m), methylsilicone capillary column (50 m) or a SPB-5 capillary column (30 m) at appropriate temperatures and integrated using a Hewlett-Packard 3390A integrator.

THF was distilled from sodium benzophenone ketyl and stored under nitrogen in an ampule. BMS, 9-BBN, α-pinene, 2,2,5,5-tetramethylpiperidine (TMP), n-butyl-lithium, t-BuOK, BF$_3$.EE, acetaldehyde, 2-methylpropionaldehyde, benzaldehyde, isovaleraldehyde, β,β-dimethylacrolein (3-methyl-2-butenal), α-methoxy-α-trifluoromethylphenylacetic acid (MTPA), and menthyl chloroformate (MCF) were all obtained from Aldrich Chemical Company, Milwaukee, Wis. MTPA was converted to the acid chloride using the literature procedure.

In the examples, the ee value was established either by capillary GC examination of diastereomeric α-methoxy-α-trifluoromethylphenylacetates (MTPA) or (−)menthylchloroformate (MCF) derivatives or by comparison of the observed optical rotation with those reported in the literature.

EXAMPLE 1

B-Isoprenyl-9-BBN 2,2,5,5-Tetramethylpiperidine (TMP)(3.5 g, 4.2 mL, 25 mmol) was added at 0° C. to a solution of n-butyllithium (10.8 mL of 2.3M solution in hexane, 25 mmol) in a mixture of THF (5.5 mL) and hexane (2.5 mL) contained in a 200 mL round-bottomed flask fitted with a side-arm and connecting tube as usual (H. C. Brown et al., *Organic Synthesis via Boranes*, Wiley Interscience: New York, 1975, Chapter 9). After 15 minutes, the solution of LiTMP was cooled to −78° C. and a solution of t-BuOK (2.8 g, 25 mmol in 15 mL THF) was added slowly to provide a clear yellow solution of the potassium salt of TMP. Subsequently, isoprene (3.7 mL, 37 mmol) was added slowly to the reaction mixture over a period of five minutes while keeping the temperature of the now red solution between −78° to −60° C. After completion of the addition, the dry ice-acetone bath was replaced by a CHCl$_3$/liquid nitrogen bath (−60° C.) and stirred for an additional 15 minutes to ensure complete metallation. The potassium salt of isoprene was recooled to −78° C. and 25 mL of a 1M solution of B-methoxy-9-BBN in THF was added slowly over a period of 5 minutes. The $^{11}$B NMR spectrum of the mixture showed a singlet at δ2.5 corresponding to an 'ate' complex which was treated with 1.33 equiv of BF$_3$.EE (4 mL, 33 mmol) at −78° C. (5 min) to provide the isoprenylborane as a thick slurry. ($^{11}$B NMR: δ78 ppm). This intermediate was used as such for isoprenylation of aldehydes.

EXAMPLE 2

(±)-2-Methyl-6-methylene-7-octen-4-ol, Racemic Ipsenol

Isovaleraldehyde (2.15 g, 2.68 mL, 25 mmol) in ether (6 mL) was added dropwise to a rapidly stirred solution of B-isoprenyl-9-BBN (Example 1), maintained at −78° C. Stirring was continued for 1 h, when the $^{11}$B NMR spectrum of an aliquot showed a peak at δ52 ppm corresponding to a borinate indicating completion of the reaction. The reaction mixture was warmed to room temperature, quenched with methanol and oxidized with alkaline H$_2$O$_2$. Work up as described by H. C. Brown, *Organic Synthesis via Boranes*, Wiley Interscience, New York, 1975, Chapter 9, followed by distillation (bp 92°-94° C./19 mm Hg) provided the title compound. Yield: 2.5 g, 65%.

EXAMPLE 3

(±)-4-Methylene-5-hexen-2-ol

Following the method of Example 2, the title compound was prepared from acetaldehyde in 65% yield. bp 67°-68° C./19 mm Hg. $^1$H NMR: (CDCl$_3$), δ: 1.2

(3H, d, J=6Hz), 2.3 (2H, m), 3.9 (1H, m), 4.8–5.3(4H, m), 6.3 (1H, dd, J=12 Hz). $^{13}$C NMR: (CDCl$_3$), δ: 22.94, 41.69, 65.96, 114.0, 118.09, 138.59, 143.25.

EXAMPLE 4

2-Methyl-5-methylene-6-hepten-3-ol

Following the method of Example 2, the title compound was prepared from 2-methylpropionaldehyde in 65% yield. bp 90°–93° C./25 mm Hg. $^1$H NMR: (CDCl$_3$), δ: 0.96 (6H, d, J=6 Hz), 1.6–2.5 (3H, m), 3.65 (1H, m), 4.9–5.3 (4H, m), 6.3 (1H, dd, J=12 Hz). $^{13}$C NMR: (CDCl$_3$), δ: 17.58, 18.67, 33.51, 36.8, 74.03, 114.13, 118.21, 138.54, 143.67.

EXAMPLE 5

3-Methylene-1-phenyl-4-penten-1-ol

Following the method of Example 2, the title compound was prepared from benzaldehyde in 60% yield. bp 70° C./1.0 mm Hg. $^1$H NMR: (CDCl$_3$), δ: 2.8 (2H, m), 4.8 (1H, br t), 5.0–5.4 (4H, m), 6.4 (1H, dd, J=12 Hz), 7.3 (5H, s).

EXAMPLE 6

2-Methyl-6-methylene-7-octen-4-ol (ipsenol)

Following the method of Example 2, the title compound was prepared at 0° C. from isovaleraldehyde in 65% yield. bp 92°–94° C./19 mm Hg. $^1$H NMR: (CDCl$_3$), δ0.88 (3H, d, J=6 Hz), 0.92 (3H, d, J=6 Hz), 1.2 (2H, m), 1.8 (2H, m), 3.72 (1H, m), 5.0–5.3 (4H, m), 6.3 (1H, dd, J=12 Hz). $^{13}$C NMR: (CDCl$_3$), δ: 22.26, 23.63, 24.87, 40.79, 46.69, 67.88, 114.59, 118.86, 139.05, 143.7.

EXAMPLE 7

2-Methyl-6-methylene-2,7-octadien-4-ol (ipsdienol)

Following the method of Example 2, the title compound was prepared from β,β-dimethylacrolein in 60% yield, bp 51°–54° C./1.5 mm Hg. $^1$H NMR: (CDCl$_3$), δ: 1.66 (3H, d, J=6 Hz), 1.72 (3H, d, J=6 Hz), 2.39 (2H, d, J=7 Hz), 4.46 (1 H, m), 4.95–5.36 (5H, m), 6.32 (1H, dd, J=12 Hz). $^{13}$C NMR: (CDCl$_3$), δ: 18.52, 25.96, 40.4, 67.05, 114.4, 119.08, 128.18, 135.58, 139.24, 149.3.

EXAMPLE 8

B-Isoprenyldiisopinocampheylborane ($^d$Ipc$_2$BIpn)

This intermediate was prepared following the method for the preparation of the achiral agent of Example 1. Isoprenylpotassium, prepared by the method of L. Brandsma et al., *J. Chem. Soc. Chem. Commun.* 1985, 1677, (25 mmol) was treated with B-methoxydiisopinocampheylborane, prepared from (+)-α-pinene (25 mmol) in THF at −78° C. $^{11}$B NMR showed a singlet at δ2 ppm corresponding to the 'ate' complex. This 'ate' complex was treated with 1.33 equiv of BF$_3$.EE (4 mL, 33 mmol) at −78° C. (5 min) to provide the title compound as a thick slurry. This was used as such for the asymmetric isoprenylation of aldehydes.

EXAMPLE 9

(R)-(+)-2-Methyl-6-methylene-7-octen-4-ol, (+)-Ipsenol

Isovaleraldehyde (2.15 g, 2.68 mL, 25 mmol) in ether (6 mL) was added dropwise to a rapidly stirred solution of B-isoprenyldiisopinocampheylborane, $^d$Ipc$_2$BIpn, maintained at −78° C. Stirring was continued for 1 h, when the $^{11}$B NMR spectrum of an aliquot showed a peak at δ52 ppm corresponding to a borinate indicating completion of the reaction. The reaction mixture was warmed to 0° C. and acetaldehyde (2.1 mL, 37.5 mmol) was added when one equiv of α-pinene was eliminated. $^{11}$B NMR showed a peak at δ32 ppm corresponding to a boronate. THF was substituted with EE and 1.1 equiv. of diethanolamine (2.6 mL, 27.5 mmol) was added and stirred for 2 h. The precipitated boron components were filtered and the filtrate was concentrated and distilled (92°–94° C./19 mm Hg) to yield 2.3 g (60%) of (+)-ipsenol. [α]$_D$= +17.3° (c 1, MeOH) which corresponds to 93.7% ee. The spectral properties were identical to the racemic mixture of Example 6.

EXAMPLE 10

(S)-(+)-2-Methyl-6-methylene-2,7-octadien-4-ol, (+)-Ipsdienol

β,β-Dimethylacrolein (2.15 g, 2.68 mL, 25 mmol) in ether (6 mL) was added dropwise to a rapidly stirred solution of B-isoprenyldiisopinocampheylborane, maintained at −78° C. Stirring was continued for 1 h, when the $^{11}$B NMR spectrum of an aliquot showed a peak at δ52 ppm corresponding to a borinate indicating completion of the reaction. The reaction mixture was warmed to 0° C. and acetaldehyde (2.1 mL, 37.5 mmol) was added when one equiv of α-pinene was eliminated. $^{11}$B NMR showed a peak at δ32 ppm corresponding to a boronate. THF was substituted with EE and 1.1 equiv of diethanolamine (2.6 mL, 27.5 mmol) was added and stirred for 2 h. The precipitated boron components were filtered and the filtrate was concentrated and distilled (51°–54° C./1.5 mm Hg) to yield 2.3 g (60%) of (+)-ipsdienol. [α]$_D$= +13.18° (c 1, MeOH) which corresponds to 96% ee. The spectral properties of (+)-ipsdienol were identical to that of the racemic mixture.

EXAMPLE 11

B-Isoprenyldiisopinocampheylborane ($^l$Ipc$_2$BIpn)

This intermediate was prepared following the method of Example 8. B-methoxydiisopinocampheylborane, prepared from (−)-α-pinene was used instead of the methoxy derivative prepared from (+)-α-pinene and the same reaction sequence followed to obtain the title compound as a thick slurry. This was used as such for the asymmetric isoprenylation of aldehydes.

EXAMPLE 12

(S)-(−)-2-Methyl-6-methylene-7-octen-4-ol, (−)-Ipsenol

Isovaleraldehyde (2.15 g, 2.68 mL, 25 mmol) in ether (6 mL) was added dropwise to a rapidly stirred solution of B-isoprenyldiisopinocampheylborane, $^l$Ipc$_2$BIpn, maintained at −78° C. Stirring was continued for 1 h, when the $^{11}$B NMR spectrum of an aliquot showed a peak at δ52 ppm corresponding to a borinate indicating completion of the reaction. The reaction mixture was warmed to 0° C. and acetaldehyde (2.1 mL, 37.5 mmol) was added when one equiv of α-pinene was eliminated. $^{11}$B NMR showed a peak at δ32 ppm corresponding to a boronate. THF was substituted with EE and 1.1 equiv. of diethanolamine (2.6 mL), 27.5 mmol) was added and stirred for 2 h. The precipitated boron components were filtered and the filtrate was concentrated and distilled (92°–94° C./19 mm Hg) to yield 2.5 g (65%) of (−)-ipsenol. [α]$_D$= −17.67° (c 1, MeOH)

which corresponds to 96% ee. The spectral properties were identical to the racemic mixture of Example 6.

EXAMPLE 13

(R)-(−)-2-Methyl-6-methylene-2,7-octadien-4-ol, (−)-Ipsdienol $\beta,\beta$-Dimethylacrolein (2.15 g, 2.68 mL, 25 mmol) in ether (6 mL) was added dropwise to a rapidly stirred solution of B-isoprenyldiisopinocampheylborane (Example 11), maintained at −78° C. Stirring was continued for 1 h, when the $^{11}$B NMR spectrum of an aliquot showed a peak at δ52 ppm corresponding to a borinate indicating completion of the reaction. The reaction mixture was warmed to 0° C. and acetaldehyde (2.1 mL, 37.5 mmol) was added when one equiv of α-pinene was eliminated. $^{11}$B NMR showed a peak at δ32 ppm corresponding to a boronate. THF was substituted with EE and 1.1 equiv of diethanolamine (2.6 mL, 27.5 mmol) was added and stirred for 2 h. The precipitated boron components were filtered and the filtrate was concentrated and distilled (51°–54° C./1.5 mm Hg) to yield 2.3 g (60%) of (−)-ipsdienol. $[\alpha]_D = -13.11°$ (c 1, MeOH) which corresponds to 96% ee. The spectral properties of (−)-ipsdienol were identical to that of the racemic mixture.

EXAMPLE 14

B-Isoprenylbis(2-isocaranyl)borane (2-Icr$_2$BIpn)

This intermediate was prepared following the method for the preparation of the isopinocampheyl reagent (example 8), B-methoxybis(2-isocaranyl)borane, prepared from (+)-2-carene. (H. C. Brown et. al. *J. Am. Chem. Soc.* 1990, 112, 2389) was used instead of the methoxy derivative from (+)-α-pinene and the same sequence followed to obtain the title compound. This was used for the asymmetric isoprenylation of aldehydes.

EXAMPLE 15

B-Isoprenylbis(4-isocaranyl)borane (4-Icr$_2$BIpn)

This intermediate was prepared following the method of Example 14. B-Methoxybis(4-isocaranyl)borane, prepared from (+)-3-carene was used instead of the methoxy derivative from (+)-2carene and the same sequence followed to obtain the title compound. This was used as such for the asymmetric isoprenylation of aldehydes.

EXAMPLE 16

(R)-(+)-2-Methyl-6-methylene-7-octen-4-ol, (+)-Ipsenol

Isovaleraldehyde (2.15 g, 2.68 mL, 25 mmol) in ether (6 mL) was added dropwise to a rapidly stirred solution of B-Isoprenyldiisopinocampheylborane, $^d$Ipc$_2$BIpn, maintained in THF/EE (1:2) at −100° C. Stirring was continued for 6 h, when the $^{11}$B NMR spectrum of an aliquot showed a peak at δ52 ppm, corresponding to a borinate indicating completion of the reaction. The reaction mixture was warmed to 0° C. and acetaldehyde (2.1 mL, 37.5 mmol) was added when one equiv of α-pinene was eliminated. $^{11}$B NMR showed a peak at δ32 ppm corresponding to a boronate. The solvents were removed in vacuo and EE (20 mL) was added, followed by 1.1 equiv. of diethanolamine (2.6 mL, 27.5 mmol). Stirring was continued for 2 h and the precipitated boron components were filtered and the filtrate concentrated. Distillation (92°–94° C./19 mm Hg) provided 2.3 g (60%) of (+)-ipsenol, $[\alpha]_D = +18.5°$ which corresponds to 100% ee. The spectral properties were identical to the sample obtained from example 9.

EXAMPLE 17

(S)-2-Methyl-6-methylene-2,7-octadien-4-ol, (+)-Ipsdienol

The title compound was prepared using $^d$Ipc$_2$BIpn (example 8) following the method for the preparation of Ipsenol (example 16). $\beta,\beta$-dimethylacrolein was used instead of isovaleraldehyde in example 16, and the same sequence followed to obtain 2.5 g (65%) of (+)-ipsdienol: bp 51°–54° C./1.5 mm Hg. $[\alpha]_D = 13.7°$ (c 1, MeOH) which corresponds to 100% ee.

EXAMPLE 18

(S)-(−)-2-Methyl-6-methylene-7-octen-4-ol, (−) Ipsenol

The title compound was prepared using a procedure similar to Example 16. B-Isoprenyldiisopinocampheylborane, prepared from (−)-α-pinene (example 11) was used instead of the one prepared from (+)-α-pinene (example 8) and the same reaction sequence in example 16 followed to obtain 2.5 g (65%) of the title compound $[\alpha]_D = -18.5°$ which corresponds to 100% ee.

EXAMPLE 19

(R)-(−)-2-Methyl-6-methylene-2,7-octadien-4-ol, (−)-Ipsdienol

The title compound was prepared following the method for the preparation of (+)-Ipsdienol (example 18). The reagent $^l$Ipc$_2$BIpn from example 11 was used and the same reaction sequence as described in example 17 followed to obtain 2.5 g (65%) of (−)-ipsdienol: bp 51°–54° C./1.5 mm Hg. $[\alpha]_D = -13.7°$ (c 1, MeOH) which corresponds to 100% ee.

EXAMPLE 20

(S)-(−)-2-Methyl-6-methylene-7-octen-4-ol, (−)-Ipsenol

Isovaleraldehyde (2.15 g, 2.68 mL, 25 mmol) in ether (6 mL) was added dropwise to a rapidly stirred solution of B-Isoprenylbis(2-isocaranyl)borane, 2-Icr$_2$BIpn (example 14) maintained in THF at −78° C. Stirring was continued for 1 h, when the $^{11}$B NMR spectrum of an aliquot showed a peak at δ52 ppm corresponding to a borinate indicating completion of the reaction. The reaction mixture was warmed to 0° C. and acetaldehyde (2.1 mL, 37.5 mmol) was added when one equiv of 2-carene was eliminated. $^{11}$B NMR showed a peak at δ32 ppm corresponding to a boronate. The solvents were removed in vacuo and EE (20 mL) was added, followed by 1.1 equiv of diethanolamine (2.6 mL, 27.5 mmol). Stirring was continued for 2 h and the precipitated boron components were filtered and the filtrate concentrated. Distillation (92°–94° C./19 mm Hg) provided 2.3 g (60%) of (−)-ipsenol, $[\alpha]_D = -18.1°$ which corresponds to 98% ee. The spectral properties were identical to the sample obtained from example 9.

EXAMPLE 21

(R)-(+)-2-Methyl-6-methylene-7-octen-4-ol, (+)-Ipsenol

The title compound was prepared by using the reagent 4-Icr$_2$BIpn (example 15) and isovaleraldehyde as in Example 19 but using −100° C. for the reaction (conditions in example 17). (+)-Ipsenol (2.5 g, 65%) was obtained after work up. $[\alpha]_D = +18.5°$ which corresponded to 100% ee.

EXAMPLE 22

(S)-2-Methyl-6-methylene-2,7-octadien-4-ol, (+)-Ipsdienol

The title compound was prepared using 2-Icr$_2$BIpn (example 14) following the method for the preparation of Ipsdienol (example 19). β,β-dimethylacrolein was used instead of isovaleraldehyde in example 21 and the same sequence followed to obtain 2.5 g (65%) of (+)-ipsdienol: bp 51°–54° C./1.5 mm Hg. $[\alpha]_D = +13.7°$ (c 1, MeOH) which corresponds to 100% ee.

EXAMPLE 23

(S)-2-Methyl-6-methylene-2,7-octadien-4-ol, (+)-Ipsdienol

The title compound was prepared using 4-Icr$_2$BIpn (example 15) following the method for the preparation of Ipsdienol (example 21). The reaction was carried out at −100° C. and the same sequence followed to obtain 2.5 g (65%) of (+)-ipsdienol: ipsdienol: bp 51°–54° C./1.5 mm Hg. $[\alpha]_D = +13.7°$ (c 1, MeOH) which corresponds to 100% ee.

Generally speaking, the processes of this invention can be run from room temperature to −100° C., but enantioselectivities improve with lower reaction temperatures. Hence, low reaction temperatures are preferred. Especially preferred are reaction temperatures from −78° to −100° C.

I claim:
1. $^d$B-2'-Isoprenyldiisopinocampheylborane.
2. $^l$B-2'-Isoprenyldiisopinocampheylborane.
3. $^d$B-2'-Isoprenyl-bis(2-isocaranyl)borane.
4. $^d$B-2'-Isoprenyl-bis(4-isocaranyl)borane.

* * * * *